United States Patent

Baysdon et al.

[11] Patent Number: 5,688,994
[45] Date of Patent: Nov. 18, 1997

[54] PROCESS FOR PREPARING N-PHOSPHONOMETHYLIMINODIACETIC ACID

[75] Inventors: Sherrol Lee Baysdon, Pacific; David Lee Taxter, St. Louis County, both of Mo.

[73] Assignee: Monsanto Company, St. Louis, Mo.

[21] Appl. No.: 768,334

[22] Filed: Dec. 17, 1996

Related U.S. Application Data

[63] Continuation of Ser. No. 474,847, Jun. 7, 1995, abandoned.

[51] Int. Cl.⁶ .................................................. C07F 9/38
[52] U.S. Cl. ................................................. 562/17
[58] Field of Search ....................................... 562/17

[56] References Cited

U.S. PATENT DOCUMENTS

| | | | |
|---|---|---|---|
| 3,288,846 | 11/1966 | Irani et al. | 260/500 |
| 3,950,402 | 4/1976 | Franz | 260/502.5 |
| 3,954,848 | 5/1976 | Franz | 260/502.5 |
| 4,724,103 | 2/1988 | Gentilcore | 260/502.5 F |
| 4,775,498 | 10/1988 | Gentilcore | 260/502.5 F |
| 4,931,585 | 6/1990 | Pelyva et al. | 562/17 |
| 5,312,973 | 5/1994 | Donadello | 562/17 |
| 5,527,953 | 6/1996 | Jones et al. | 562/17 |

FOREIGN PATENT DOCUMENTS

| | | | |
|---|---|---|---|
| 2090873 | 12/1971 | France | C07F 9/00 |
| 1142294 | 2/1966 | United Kingdom | C07F 9/38 |
| 2154588 | 2/1984 | United Kingdom | C07F 9/38 |

*Primary Examiner*—C. Warren Ivy
*Assistant Examiner*—Jean F. Vollano
*Attorney, Agent, or Firm*—Grace Bonner Monsanto Company; Arnold, White & Durkee

[57] ABSTRACT

A process for the preparation of N-phosphonomethyliminodiacetic acid is disclosed. The process comprises simultaneously infusing into a reaction mixture water, a source of iminodiacetic acid, a source of formaldehyde, and a source of phosphorous acid and strong acid.

23 Claims, No Drawings

PROCESS FOR PREPARING N-PHOSPHONOMETHYLIMINODIACETIC ACID

This application is a continuation application of U.S. patent application Ser. No. 08/474,847 filed Jun. 7, 1995, now abandoned.

BACKGROUND OF THE INVENTION (1) Field of the Invention

The present invention relates to method for the phosphonomethylation of primary or secondary amines and more particularly to an improved process for preparing N-phosphonomethyliminodiacetic acid.

(2) Description of the Related Art

The compound, N-phosphonomethyliminodiacetic acid (NPMIDA), serves as an intermediate in the preparation of N-phosphonomethylglycine (glyphosate), which is an important broad spectrum herbicide. The structure of NPMIDA is shown in formula I:

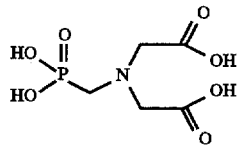

In the past, NPMIDA has been prepared from a source of iminodiacetic acid (IDA) using multistep processes. Typically, iminodiacetonitrile (IDAN) is first hydrolyzed with an alkali metal base to form the dialkali metal salt of iminodiacetic acid (IDA). Both the alkali metal salts of IDA and IDA itself are used to prepare NPMIDA. The IDA is typically isolated from the hydrolysate of IDAN by acidification with a mineral acid (typically sulfuric or hydrochloric acid), crystallization of the IDA, and filtration to recover the IDA. The IDA is then used to prepare NPMIDA. For example, in U.S. Pat. No. 3,288,846, which is incorporated by reference, Irani et al. first formed the hydrochloride salt of IDA from IDA followed by phosphonomethylation with phosphorous acid and formaldehyde.

In U.S. Pat. Nos. 4,724,103 and 4,775,498, which are incorporated by reference, Gentilcore disclosed a method that used the disodium salt of IDA (DSIDA) as starting material for the phosphonomethylation. The DSIDA was reacted in series first with hydrochloric acid to form the hydrochloride salt of IDA (IDA.HCl) followed by phosphonomethylation with phosphorous acid and formaldehyde to form NPMIDA. Phosphorus trichloride served as the source of both the hydrochloric acid and the phosphorous acid.

In the first, hydrolysis step, phosphorus trichloride was hydrolyzed to phosphorous acid while DSIDA was simultaneously transformed to IDA.HCl and sodium chloride according to the following general equations:

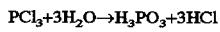

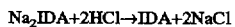

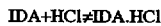

In the second, phosphonomethylation step, formaldehyde was added to the reaction mixture to phosphonomethylate the IDA.HCl according to the following equation:

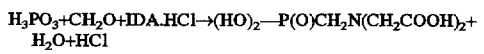

In Example 2 of the '103 and '498 patents, the two-step method was modified by combining a portion of the DSIDA and all of the $PCl_3$ in the first step and then, in the second reaction step, adding formalin to phosphonomethylate and also adding more $Na_2IDA$ so that at least some of the IDA.HCl formation occurred in the second reaction mixture simultaneous with the phosphonomethylation reaction. Nevertheless, none of the $PCl_3$ was infused simultaneously with the DSIDA and formalin.

In the existing batch processes for the manufacture of NPMIDA, all of the phosphorous acid and the strong acid catalyst and the bulk of the IDA are present before the formalin and the remaining IDA are added. This approach, which was disclosed in the '103 and '498 patents as well as the approach in the '846 patent have provided useful commercial processes that achieve the desired phosphonomethylation of the IDA to NPMIDA while minimizing the undesired side reactions which would yield N-methyl iminodiacetic acid (NMIDA) and hydroxymethylphosphonic acid (HMPA). Nevertheless, the conventional method could be improved by the development of a single-stage process in which all materials are added in one reaction mixture. Such a process could be adapted to a continuous synthesis of NPMIDA and would provide a method that would simplify the production of NPMIDA and reduce the cost, the energy consumption and the amount and complexity of manufacturing equipment required while providing a high level of product yield and minimal levels of undesirable byproducts.

SUMMARY OF THE INVENTION

In accordance with the present invention, it has been discovered that N-phosphonomethyliminodiacetic acid can be produced from a source of IDA by a single-stage process using a method comprising combining in a reaction mixture water, a source of IDA, a source of formaldehyde, a source of phosphorous acid and a source of strong acid wherein the source of formaldehyde and the source of phosphorous acid are simultaneously infused into the reaction mixture. Surprisingly, this simplified one-stage process achieves the desired phosphonomethylation reaction in high yield with minimal byproduct formation. The addition of the source of the phosphorous acid at substantially the same rate that the source of the formaldehyde is infused reduces the amount of phosphorous acid present in the reaction mixture compared to that present in the currently used two stage process. The lower concentration of phosphorous acid in the reaction mixture of the present process serves to decrease the amount of HMPA and NMIDA produced as undesirable byproducts.

Thus, using the process described in more detail below, the yield of N-phosphonomethyliminodiacetic acid is found to be unexpectedly high with minimal production of undesirable byproducts.

Moreover, the present method can use a number of starting materials as sources of IDA including the disodium salt of IDA, the monosodium salt of IDA, IDA itself or a strong mineral acid salt of IDA.

The present invention can also be used in a continuous process in which the NPMIDA is continuously removed from the reaction mixture while the reactants are continually added to the reaction mixture.

Thus, included among the several advantages provided by the present invention are the provision of a method for the synthesis of NPMIDA in a single-stage process that is more cost and energy efficient; the provision for a method for producing NPMIDA that is simpler and requires less manufacturing equipment; the provision of a method for producing NPMIDA in high yield without a substantial amount of byproduct production; and the provision of a method for the continuous production of NPMIDA.

DESCRIPTION OF THE PREFERRED EMBODIMENTS

The process of this invention provides a method whereby a primary or a secondary amine can be phosphonomethylated using a mixture of water, phosphorous acid, a strong acid, formaldehyde and the primary or secondary amine. In particular, N-phosphonomethyliminodiacetic acid can be produced by combining in a reaction mixture, water, a source of phosphorous acid, a source of strong acid, a source of iminodiacetic acid and a source of formaldehyde wherein the source of formaldehyde and the source of phosphorous acid are simultaneously infused into the reaction mixture.

The reactions taking place are exemplified in equations I–IV above using as starting materials water, DSIDA, formaldehyde and $PCl_3$, which serves as a source of phosphorous acid and a source of strong acid. These reactants are exemplary only and are not intended in a limiting sense. Furthermore, although the process of this invention is generally described herein as using DSIDA, other suitable sources of IDA can also be used.

One of the goals achieved by the present one-stage process is the production of NPMIDA in high yield while minimizing the production of undesirable byproducts.

One undesirable byproduct is HMPA, which is formed by the reaction of phosphorous acid with formaldehyde. The amount of HMPA formed is decreased by decreasing the relative amount of phosphorous acid present. The present process is believed to achieve a reduction in HMPA formation by maintaining a lower concentration of phosphorous acid during the course of reaction.

The process in the present invention also diminishes the relative production of HMPA by increasing the amount of free HCl reactant present in the reaction mixture. The process in the present invention provides for a gradual infusion of either the HCl or $PCl_3$ as a source of HCl over the same period of time that the other reactants are added. It is thereby possible to avoid the immediate production and mitigate the loss of excess HCl that evolves. As a result, a higher concentration of free HCl is maintained throughout the reaction period. This in turn favors the formation of NPMIDA. Such an increase in the production of NPMIDA increases the relative production of NPMIDA with respect to the byproduct HMPA.

Under certain conditions IDA and formaldehyde can react to form another undesirable byproduct, NMIDA. Production of NMIDA is minimized by maintaining sufficiently high levels of strong mineral acid, preferably HCl, in the reaction mixture. The strong acid serves several functions. First, as shown in equation II above, the strong acid, preferably hydrochloric acid, produces the acid form of IDA when an alkali metal salt of IDA is used as a starting material source of IDA. Second, the strong acid converts the IDA to the mineral acid salt of IDA as shown in equation III when either an alkali metal salt of IDA or IDA itself is used as a starting material. A third function of the strong acid is to minimize the production of the undesired byproduct, N-methyl iminodiacetic acid (NMIDA). Applicants have discovered that all three of these functions of the strong acid are advantageously achieved by infusing a phosphorus halide or a mixture of a strong acid with phosphorous acid simultaneously with the source of IDA and formaldehyde.

Using HCl as the strong mineral acid, the concentration of free HCl in the reaction mixture is in the range of from about 0% to about 20%, preferably at least about 5 wt % calculated on the basis of HCl and $H_2O$ only. As noted above, the process in the present invention maintains a high concentration of free HCl in the reaction mixture as a result of the infusion of the HCl over the same period of time that the other reactants are added. This maintained high level of acid results in less production of the undesirable byproduct, NMIDA.

By infusing the source of phosphorous acid, it is possible to avoid production of high concentrations of phosphorous acid in the reaction mixture. This reduces the amount of byproduct produced, in particular HMPA and NMIDA.

The present process, therefore, allows for high yields of NPMIDA and low amounts of byproducts while successfully achieving a one-stage synthetic process. Yields are calculated as the ratio of the number of moles produced divided by quantity of the number of moles of the starting source of IDA minus the number of moles of IDA recovered after the end of reaction. Greater than 90% yields of NPMIDA can be achieved using the present method.

It is desirable that the phosphorous acid and strong acid be provided to the reaction mixture from a single source, preferably, a phosphorus halide. Most preferred is $PCl_3$, which forms phosphorous acid and hydrochloric acid upon reaction with water according to the mechanism set forth in equation I. Alternatively, phosphorus acid and a strong acid such as sulfuric acid or hydrochloric acid can be added simultaneously to provide the reactants for forming an acid salt of IDA and for phosphonomethylation (equations II–IV).

As used herein the terms "strong acid" or "strong mineral acid" include inorganic mineral acids having a $pK_a$ less than about 2. Typically such acids include sulfuric acid, hydrochloric acid, hydrobromic acid, hydroiodic acid and the like. Preferred as a source of strong acid is hydrochloric acid although any suitable strong mineral acid can be employed in its place.

As noted above the present method can use several starting materials as sources of IDA, for example, the disodium salt of IDA (DSIDA), the monosodium salt of IDA, IDA itself or a strong mineral acid salt of IDA. The source of formaldehyde can include formaldehyde gas, an aqueous solution of formaldehyde gas (formalin) or paraformaldehyde. A preferred source of formaldehyde is formalin.

In general, the process of the present invention can be carried out at temperatures of from about 85° C. to about 200° C. and under pressure conditions of from about 0 to about 60 psig above ambient pressure. By ambient conditions, reference is made to the temperature and pressure in the surrounding air, i.e. approximately room temperature and a standard atmosphere of pressure. It is preferred that the temperature range be from about 105° C. to about 145° C. Most preferred is a temperature range of from about 125° C. to about 145° C. Under ambient pressure, reflux temperatures are from about 105° to about 115° C. It is preferred for the present process, however, that the reaction be run under increased pressure of from about 5 to about 60 psig. Most preferred is a pressure from about 15 to about 30 psig. The increased reaction temperature and increased pressure above ambient pressure gives a higher yield of NPMIDA while producing less of the byproduct, NMIDA.

When $PCl_3$ is used as a source of phosphorous acid, the hydrolysis of $PCl_3$ as shown in equation I is an exothermic reaction. The hydrolysis reaction can, therefore, provide a source of heat for maintaining the desired reaction temperature. This provides a cost savings inasmuch as the amount of heat required from an outside source would be decreased.

The simultaneous delivery of reactants to the reaction mixture allows conversion of IDA to NPMIDA in high yield with minimal production of undesirable byproducts. By simultaneous infusion or simultaneous delivery, it is meant that addition of the reactants is over approximately the same time period. One skilled in the art would readily appreciate that this can be accomplished by a continuous infusion of reactants or by adding reactants in alternate and repeated quantities or by any other suitable means so long as the reactants are added to the reaction mixture during the phosphonomethylation reaction.

In general, it is desirable that the rate of delivery of each of the reactants be substantially the same calculated on a mole basis relative to time. By substantially the same rate it is meant for example, that when all reactants are added simultaneously, that the source of phosphorous acid, the source of strong acid and the source of formaldehyde are delivered into the reaction mixture each at a rate in moles per unit time that can be independently from about 80% to about 140% of the rate of delivery of the source of IDA.

In one of the preferred embodiments, the reaction vessel can be initially charged with about 25% to about 75% of the total source of IDA to be added to the reaction vessel. Where an initial amount of the source of IDA is added to the reaction vessel, the rate of delivery of the source of IDA thereafter can be from about 25% to about 125% of the rate of delivery of the source of phosphorous acid or the source of formaldehyde on a mole basis. In a variation of this embodiment, the reaction vessel can be charged with an initial amount of a source of IDA in combination with an initial amount of a source of phosphorous acid. In a further variation of this embodiment the reaction vessel can be initially charged with a strong acid.

Following the reaction, NPMIDA is recovered from the reaction mixture. Precipitation of NPMIDA can be facilitated by cooling. In order to recover further amounts from the reaction liquid, a dilute base such as sodium hydroxide can optionally be added to the reaction mixture to adjust the pH to the point of minimum solubility of NPMIDA. The water from the dilute base serves to solubilize NaCl produced from reaction of the base. The amount of base required is approximately equal to the HCl in the reaction mixture and is readily calculated by one skilled in the art.

The process in the present invention can be utilized in any reactor system known in the art including batch reactors, continuous reactors or semicontinuous reactors. In a batch reactor, all the reactants are added and the reactions allowed to proceed during which time no product is withdrawn. In a continuous reactor the reactants are introduced and products withdrawn simultaneously in a continuous manner. In a semicontinuous reactor some of the reactants can be charged at the beginning, whereas the remaining are fed continuously as the reaction progresses.

The present invention can thus be advantageously used in a continuous or semicontinuous reactor system such as, for example, in a tank reactor. In such a system the reactor may optionally be initially charged with the DSIDA (or other source of IDA) and $PCl_3$ followed by a continuous feed of DSIDA (or other source of IDA), $PCl_3$, formaldehyde and water. After allowing an initial period for reaction to take place, a fraction of the reaction mixture is withdrawn from the tank reactor as an effluent on a continuous basis. The effluent can be cooled and, optionally, the pH can be adjusted to further precipitate the compound from the liquid. The precipitate is then separated and recovered from the mother liquor. One skilled in the art will appreciate that numerous well known methods can be used to recover the NPMIDA precipitate. For example, the precipitate can be separated from the mother liquor by continuous filtration (see *Chemical Engineers' Handbook*, 6th Ed. , Perry and Green, eds., McGraw-Hill, New York, chapter 19, pp. 1–108, 1984 which is incorporated by reference). When, DSIDA is used as starting material or when a base such as sodium hydroxide is added to facilitate precipitation, a salt is produced in the mother liquor which must, therefore, be discarded. However, when IDA is used as a starting material and base is not added to aid in the recovery of dissolved NPMIDA, the mother liquor can be returned to the reactor. This recycles any NPMIDA remaining in the mother liquor back to the reaction mixture and ultimately allows a greater recovery of NPMIDA from the process.

The above disclosure generally describes the process of the prevent invention. A more complete understanding can be obtained by reference to the following specific examples, which describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

This example illustrates the preparation of NPMIDA from DSIDA, $PCl_3$, formaldehyde and water under increased pressure and high temperature with an initial charging of the reaction vessel with DSIDA and $PCl_3$.

To a 2 liter jacketed kettle reactor equipped with condenser and mechanical stirring was charged 512 g of an aqueous solution (41.5%) of iminodiacetic acid disodium salt. The reactor was brought to an internal temperature of 85° C. and $PCl_3$ (173 g) was added via dip tube over 28 minutes. The resulting mixture was transferred to a 2 liter reactor system with pressure and temperature control and brought to 85° C. An additional 65 g of $PCl_3$ was charged to the reactor. Temperature in the reactor was raised to 130° C. (12.5 psig) and the simultaneous feeds of $PCl_3$ (199 g over 44 min.), 43.3% aqueous formaldehyde (219 g over 60 minutes), and 41.5% aqueous iminodiacetic acid disodium salt (769 g over 54 minutes) to the reactor were initiated. During this portion of the reaction, the temperature in the reactor reached a maximum of 131° C. and the pressure was allowed to rise to 25 psig and held there. After completion of all of the feeds the reaction was allowed to proceed for 60 minutes, then cooled and filtered to afford 596 g of 99.6% N-phosphonomethyliminodiacetic acid. The filtrate contained an additional 25 g of N-phosphonomethyliminodiacetic acid and 27 g of iminodiacetic acid. This is a 97% yield of N-phosphonomethyliminodiacetic acid based on unrecovered iminodiacetic acid disodium salt.

EXAMPLE 2

This example illustrates the preparation of NPMIDA from DSIDA, $PCl_3$, formaldehyde and water under ambient pressure and reflux temperatures with an initial charging of the reaction vessel with DSIDA and $PCl_3$.

To a 2 liter jacketed kettle reactor equipped with condenser and mechanical stirring was charged 501 g of an aqueous solution (42.4%) of iminodiacetic acid disodium salt. The reactor was brought to an internal temperature of 85° C. and $PCl_3$ (175 g) was added via dip tube over approximately 30 minutes. Temperature in the reactor was raised to reflux (about 110° C.) and the simultaneous feeds of $PCl_3$ (116 g over 24 min.), 43.6% aqueous formaldehyde (165 g over 62 minutes), and 42.4% aqueous iminodiacetic acid disodium salt (334 g over 56 minutes) to the reactor were initiated. During this portion of the reaction, the temperature in the reactor was maintained at reflux. After completion of all of the feeds followed by a 60 minute hold time, the reaction was cooled and filtered to afford 377 g of 98.3% N-phosphonomethyliminodiacetic acid. The filtrate contained an additional 30 g of N-phosphonomethyliminodiacetic acid and 12 g of iminodiacetic acid. This is a 95% yield of N-phosphonomethyliminodiacetic acid based on unrecovered iminodiacetic acid disodium salt.

EXAMPLE 3

This example illustrates the preparation of NPMIDA from DSIDA, $PCl_3$, formaldehyde and water following an initial charging of the reaction vessel with HCl.

To a 2 liter jacketed kettle reactor equipped with condenser and mechanical stirring was charged 50 g of 37% HCl. The solution was heated to reflux and a simultaneous feed of iminodiacetic acid disodium salt (832.5 g of 42.5% aqueous solution), formalin (140.5 g of 47% material), and $PCl_3$ (283 g) was begun. The iminodiacetic acid disodium salt was fed over a period of 64 minutes, $PCl_3$ over 53 minutes, and formalin over 63 minutes. After completion of all of the feeds followed by a 60 minute hold time at reflux, the reaction was cooled and filtered to afford 361 g of 98.5% N-phosphonomethyliminodiacetic acid. The filtrate contained an additional 19 g of N-phosphonomethyliminodiacetic acid and 27 g of iminodiacetic acid. This is a 93% yield of N-phosphonomethyliminodiacetic acid based on unrecovered iminodiacetic acid disodium salt.

EXAMPLE 4

This example illustrates a repeated preparation in water of NPMIDA from IDA, $PCl_3$ and formaldehyde with an initial charging of the reaction vessel with IDA, HCl and water; removal of NPMIDA after reaction; and recharging of the mother liquor with IDA.

To a 2 liter jacketed kettle reactor equipped with condenser and mechanical stirring was charged 266 g of iminodiacetic acid, 194 g of concentrated HCl, and 358 g of $H_2O$. The solution was heated to 103° C. and simultaneous feeds of $PCl_3$ and formalin were initiated. $PCl_3$ (291 g) was fed over a period of 50 minutes and formalin (153 g of 47% material) was fed over a period of 60 minutes. After completion of all of the feeds followed by a 60 minute hold time at reflux, the reaction was cooled and filtered to afford a solid mass of N-phosphonomethyliminodiacetic acid. The resulting filtrate was fortified with an additional 266 g of iminodiacetic acid and $PCl_3$ and formalin were fed in the manner and quantity outlined above. After completion of all of the feeds followed by a 60 minute hold time at reflux, the reaction was cooled and filtered. The combined cake mass from the two reactions totaled 678 g and was 98% N-phosphonomethyliminodiacetic acid by weight. The mother liquors from above contained 123 g of N-phosphonomethyliminodiacetic acid and 34 g of iminodiacetic acid. This is a 94% yield of N-phosphonomethyliminodiacetic acid based on unrecovered iminodiacetic acid.

Thus, the process of the present invention as illustrated in examples 1–4 gave high yields of from 93% to 97% using the one-stage process of the present invention.

In view of the above, it can be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A process for preparing N-phosphonomethyliminodiacetic acid comprising combining in a reaction mixture water, a source of iminodiacetic acid, a source of formaldehyde, and a phosphorus trihalide wherein the source of formaldehyde and the phosphorus trihalide are simultaneously infused into the reaction mixture, to form said N-phosphonomethyliminodiacetic acid.

2. A process according to claim 1 wherein the water, the source of iminodiacetic add, the source of formaldehyde, and the phosphorus trihalide are simultaneously infused.

3. A process according to claim 1 wherein the source of iminodiacetic acid is selected from the group consisting of iminodiacetic acid, a strong mineral acid salt of iminodiacetic acid, an alkali metal salt of iminodiacetic acid, and combinations thereof.

4. A process according to claim 3 wherein the source of iminodiacetic acid is the monosodium salt of IDA.

5. A process according to claim 3 wherein the source of iminodiacetic acid is the disodium salt of IDA.

6. A process according to claim 3 wherein the source of formaldehyde is selected from the group consisting of formaldehyde gas, an aqueous solution of formaldehyde and paraformaldehyde.

7. A process according to claim 6 wherein the source of formaldehyde is an aqueous solution of formaldehyde.

8. A process according to claim 3 wherein the phosphorus trihalide is phosphorus trichloride.

9. A process according to claim 3 wherein the process further comprises continuously removing N-phosphonomethyliminodiacetic acid from the reaction mixture.

10. A process according to claim 2 wherein the source of iminodiacetic acid, the source of formaldehyde, and the phosphorus trihalide are infused at substantially the same rate.

11. A process according to claim 1 wherein prior to infusing, the process further comprises adding a source of IDA.

12. A process according to claim 1 wherein prior to infusing, the process further comprises adding a strong acid and/or a phosphorus trihalide.

13. A process according to claim 1 wherein the reaction mixture is maintained under a pressure that is increased above ambient pressure.

14. A process according to claim 13 wherein the pressure is from about 15 to about 30 psig.

15. A process according to claim 1 wherein the reaction mixture is maintained at a temperature above ambient temperature.

16. A process according to claim 15 wherein the temperature is from about 105° C. to about 145° C.

17. A process according to claim 1 wherein the yield of N-phosphonomethyliminodiacetic acid is greater than 90%.

18. A process for preparing N-phosphonomethyliminodiacetic Acid comprising combining in a reaction mixture water, a source of iminodiacetic acid, a source of formaldehyde, a source of phosphorous acid and a source of strong acid wherein the source of formaldehyde and the source of phosphorous acid are simultaneously infused into file reaction mixture, to form said N-phosphonomethyliminodiacetic Acid.

19. A process according to claim 18 wherein the source of phosphorus acid is the hydrolysis product of a phosphorus trihalide in water.

20. A process of claim 18 wherein the reactants are continuously added to a reactor and the product is continuously withdrawn.

21. A process of claim 18 wherein the source of iminodiacetic acid is the monosodium salt of said acid.

22. A process of claim 18 wherein the source of iminodiacetic acid is the diosodium salt of said acid.

23. A process of claim 18 wherein the hydrolysis product contains sulfuric acid as the strong acid.

* * * * *

UNITED STATES PATENT AND TRADEMARK OFFICE
CERTIFICATE OF CORRECTION

PATENT NO.   :   5,688,994
DATED        :   November 18, 1997
INVENTOR(S)  :   Sherrol L. Baysdon and David L. Taxter It is certified that error appears in the above-identified patent and that said Letters Patent is hereby corrected as shown below:

Column 1, line 61, please delete "≠" and insert therefor -- ≉ --.

In claim 18, column 9, line 9, before "reaction" and following "into", please delete "file" and insert therefor --the--.

Signed and Sealed this

Seventeenth Day of March, 1998

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,688,994
DATED : November 18, 1997
INVENTOR(S) : Sherrol L. Baysdon and David L. Taxter It is certified that error appears in the above-identified patent and that said Letters Patent is hereby corrected as shown below:

In claim 2, column 8, line 25, before "the" and following "iminodiacetic", please delete "add" and insert therefor --acid--.

Signed and Sealed this

Sixth Day of April, 1999

Attest:

Q. TODD DICKINSON

Attesting Officer

Acting Commissioner of Patents and Trademarks